US008603491B2

(12) United States Patent
Leberre et al.

(10) Patent No.: US 8,603,491 B2
(45) Date of Patent: Dec. 10, 2013

(54) CDNA CONSTRUCT OF SALMONIDAE ALPHAVIRUS

(75) Inventors: Monique Leberre, Montigny-le-Bretonneux (FR); Coralie Moriette, Le Perreux sur Marne (FR); Michel Bremont, Choisy-le-Roi (FR)

(73) Assignee: Institut National de la Recherche Agronomique, Paris (FR)

( * ) Notice: Subject to any disclaimer, the term of this patent is extended or adjusted under 35 U.S.C. 154(b) by 939 days.

(21) Appl. No.: 11/993,676

(22) PCT Filed: Jun. 21, 2006

(86) PCT No.: PCT/FR2006/001405
§ 371 (c)(1),
(2), (4) Date: Jul. 8, 2008

(87) PCT Pub. No.: WO2006/136704
PCT Pub. Date: Dec. 28, 2006

(65) Prior Publication Data
US 2008/0317777 A1  Dec. 25, 2008

(30) Foreign Application Priority Data
Jun. 21, 2005  (FR) ..................... 05 06275

(51) Int. Cl.
*A61K 39/193*   (2006.01)

(52) U.S. Cl.
USPC ............. 424/218.1; 424/184.1; 435/4; 435/5; 435/6.1

(58) Field of Classification Search
None
See application file for complete search history.

(56) References Cited

U.S. PATENT DOCUMENTS 5,631,115 A * 5/1997 Ohtsuka et al. ............ 435/91.31
6,482,634 B1 * 11/2002 Wilson et al. ............... 435/235.1
6,566,093 B1 * 5/2003 Liljestrom et al. .......... 435/69.1
2004/0258707 A1 12/2004 Weston et al.

FOREIGN PATENT DOCUMENTS

WO  WO 02/18585  *  3/2002

OTHER PUBLICATIONS

Villoing et al., An RT-PCR-based method for the diagnosis of the sleeping disease virus in experimentally and naturally infected salmonids, 2000, Diseases of Aquatic Organisms, vol. 40, pp. 19-27.*
Graham et al., First isolation of sleeping disease virus from rainbow trout, Oncorhynchus mykiss (Walbaum), in the United Kingdom, 2003, Journal of Fish Diseases, vol. 26, No. 11-12, pp. 691-694.*
Cristian Smerdou, et al., "Non-Viral Amplification Systems for Gene Transfer: Vectors Based on Alphaviruses", Current Opinion in Molecular Therapeutics, vol. 1, No. 2, XP 009062410, pp. 244-251, 1999.
Christopher J. McCormick, et al., "Introduction of Replication-Competent Hepatitis C Virus Transcripts Using a Tetracycline-Regulable Baculovirus Delivery System", Journal of General Virology, vol. 85, No. 2, XP 002369434, pp. 429-439, 2004.
Ilya Frolov, et al., "Alphavirus-Based Expression Vectors: Strategies and Applications", Proc. Natl. Acad. Sci. USA, vol. 93, No. 21, XP 000910193, pp. 11371-11377, 1996.
Duane E. Ruffner, et al., "Sequence Requirements of the Hammerhead RNA Self-Cleavage Reaction", Biochemistry, vol. 29, No. 47, XP 002369435, pp. 10695-10702, 1990.
Richard Shippy, et al., "The Hairpin Ribozyme: Discovery, Mechanism, and Development for Gene Therapy", Molecular Biotechnology, vol. 12, No. 1, XP 009062409, pp. 117-129, 1999.
Jonathan Weston, et al., "Comparison of Two Aquatic Alphaviruses, Salmon Pancreas Disease Virus and Sleeping Disease Virus, by Using Genome Sequence Analysis, Monoclonal Reactivity, and Cross-Infection", Journal of Virology, vol. 76, No. 12, XP 002369436, pp. 6155-6163, 2002.
Stephane Villoing, et al., "Rainbow Trout Sleeping Disease Virus Is an Atypical Alphavirus", Journal of Virology, vol. 74, No. 1, XP 002369437, pp. 173-183, 2000.
Coralie Moriette, et al., "Recovery of a Recombinant Salmonid Alphavirus Fully Attenuated and Protective for Rainbow Trout", Journal of Virology, vol. 80, No. 8, XP 009076629, pp. 4088-4098, 2006.
U.S. Appl. No. 12/828,739, filed Jul. 1, 2010, Leberre, et al.

* cited by examiner

Primary Examiner — Benjamin P Blumel

(57) ABSTRACT

The invention concerns recombinant DNA's comprising cDNA of genomic RNA of a Salmonidae alphavirus preceded by a spacer sequence, under the control of a suitable promoter. Said recombinant DNA's are useful for obtaining expression vectors, producing recombinant Salmonidae alphavirus, and for obtaining vaccines.

14 Claims, 10 Drawing Sheets

Figure 2A:
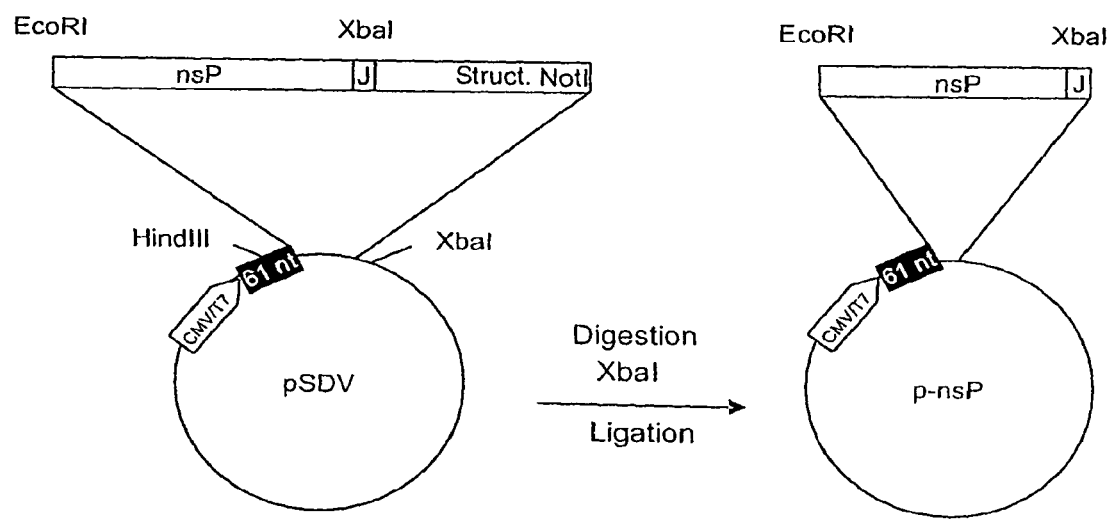

Figure 1 jour 5 jour 7 jour 10

Figure 6

A

B

CDNA CONSTRUCT OF SALMONIDAE ALPHAVIRUS

CROSS-REFERENCE TO RELATED APPLICATIONS

The present application is a 35 U.S.C. §371 National Stage patent application of International patent application PCT/FR06/001405, filed on Jun. 21, 2006, which claims priority to French patent application FR 0506275, filed on Jun. 21, 2005.

The present invention relates to the obtaining of infectious cDNAs of Salmonidae alphavirus, and to the uses of these cDNAs.

Alphaviruses are enveloped, positive-strand RNA viruses of the Togaviridae family.

Two representatives of Salmonidae alphaviruses are currently known: the sleeping disease virus (SDV), which is pathogenic for trout, and the pancreas disease virus (PDV), which is pathogenic for salmon. These two viruses, which are genetically very close, have been assigned to the alphavirus family on the basis of the similarity of the organization of their genome with that of the known alphaviruses; however, their nucleotide sequence, and also the polypeptide sequence which is deduced therefrom, exhibit only a low degree of homology with the other alphaviruses (VILLOING et al., J. Virol. 74, 173-183, 2000; WESTON et al., Virology, 256, 188-195, 1999; WESTON et al., J. Virol. 76, 6155-63, 2002); they are therefore considered to represent an alphavirus subgroup different from the mammalian alphaviruses.

The alphavirus genome encodes 2 polyproteins: the 5' portion of the coding sequence, which represents approximately two thirds thereof, encodes a polyprotein which, after proteolytic cleavage, gives the nonstructural proteins (nsP) nsP1, nsP2, nsP3 and nsP4, involved in replication of the virus; the end third of the genome encodes a polyprotein whose proteolytic cleavage produces the structural proteins (Struct): the capsid protein (C) and 2 envelope glycoproteins (E3-E2 and 6K-E1). The coding regions for the nsPs and the Structs are separated by a noncoding region called junction region (J). Two noncoding regions are also present at the 5' and 3' ends of the genome. This genome also has a cap at the 5' end and a polyA tail at the 3' end (STAUSS and STRAUSS, Microbiol. Rev., 58, 491-562, 1994).

In the Salmonidae alphaviruses, this genomic organization is conserved: the main differences with the genome of the other alphaviruses are, in addition to the low coding sequence homology, the size of the 5' and 3' noncoding regions, which are shorter in the Salmonidae alphaviruses.

The pathologies caused by SDV and PDV currently constitute an increasing problem for salmon farming. These viruses are now becoming endemic in Europe and have made their appearance on the North American continent.

The method of protecting the Salmonidae against these viral agents lies in the use of vaccines. Immunization can be carried out in various ways, depending on the species and the age of the fish to be immunized. It may be carried out, for example, by balneation. This immunization approach, which is very effective and relatively inexpensive, is the method of choice for immunization with live attenuated viruses. The immunization can also be carried out by injection of live attenuated viruses, or of inactivated viruses. Although it is more expensive than immunization by balneation, this method can be used for immunizing fish of 10 grams or more, and is thus in particular suitable for the immunization of species such as sea trout or salmon. Advantageously, it is also possible to combine a primary immunization by balneation in the presence of live attenuated viruses with a booster immunization by injection of live attenuated viruses or of inactivated viruses.

Manipulation of the genome of RNA viruses, in particular in order to generate attenuated strains, requires the availability of an infectious cDNA system, i.e. of a complete DNA copy of the RNA genome of these viruses (approximately 12000 bases), capable of being transcribed in a host cell so as to generate a viral RNA that can replicate in this cell.

Conventionally, in order to produce an infectious cDNA for alphaviruses, the cDNA of the complete viral genome, fused at the 5' end to an SP6 or T7 promoter sequence, is cloned into a plasmid. This plasmid construct is cleaved at the 3' end with a restriction enzyme, and then used in an in vitro transcription system in order to synthesize a genomic RNA using SP6 or T7 RNA polymerase. This RNA is transfected into cells sensitive to the virus in question. After a few days, newly formed virus is released into the culture supernatant. It has thus been possible to obtain infectious cDNAs for a large number of alphaviruses, for example for SV (Sindbis virus; RICE et al., J. Virol, 61, 3809-3819, 1987), SFV (Semliki Forest Virus; LILJESTROM et al., J. Virol, 65, 4107-4113, 1991), the VEE virus (Venezuelan equine encephalitis virus; DAVIS et al., Virology, 171, 189-204, 1989) and the EEE virus (eastern equine encephalitis virus; SCHOEPP et al., Virology, 302, 299-309, 2002).

However, in the case of Salmonidae alphaviruses, the attempts made to generate an infectious cDNA using this approach have failed.

The inventors have discovered that this problem can be solved by introducing a random additional sequence, acting as a spacer, between the SP6 or T7 promoter and the start of the viral genome. The addition of this sequence makes it possible to generate, in vitro, a genomic RNA which, by transfection into fish cells, allows the synthesis of the nonstructural proteins.

To generate an infectious RNA, the inventors have replaced the random sequence acting as spacer with a hammerhead ribozyme sequence. They have observed that the RNA neosynthesized from this construct is accurately cleaved at the first nucleotide of the genomic RNA of the alphavirus. The RNA thus obtained has the ability to synthesize the nsP proteins, to be replicated, to allow the synthesis of a subgenomic RNA encoding the structural proteins, and, finally, to be encapsidated so as to generate infectious viral neoparticles.

The inventors have also used this construct to insert a heterologous sequence, under the control of the subgenomic promoter of SDV. They have observed that this sequence is expressed in the cells infected with the construct, and that the viral genome comprising this sequence can be encapsidated normally in the viral particles.

A subject of the present invention is a recombinant DNA derived from the genome of a Salmonidae alphavirus, and comprising:
  a transcription promoter and, downstream of said promoter and under transcriptional control thereof;
  a spacer sequence of at least 5 nucleotides, preferably from 10 to 100 nucleotides;
  the cDNA of the genomic RNA of a Salmonidae alphavirus.

The transcription promoter may be any promoter recognized by an RNA polymerase expressed in the host cell. It may, for example, be a bacteriophage promoter, such as the T7 promoter, the T3 promoter or the SP6 promoter; in this case, the recombinant DNA in accordance with the invention must be used in combination with a construct expressing an RNA polymerase which recognizes this promoter.

A promoter recognized by an endogenous RNA polymerase of the host cell, in particular by RNA polymerase II, may also be used. It may be a viral promoter, for example one of those normally used for the expression of heterologous genes in mammalian cells, such as the CMV (cytomegalovirus) promoter, the RSV (Rous Sarcoma Virus) promoter, the SV40 early promoter, the MOMLV (Moloney Murine Leukemia Virus) promoter, etc; it may also be a eukaryotic promoter, for example a fish promoter, such as that described by ALONSO et al. (Vaccine, 21, 1591-100, 2003).

The function of the spacer sequence is to distance the promoter from the start of the alphavirus genome; its sequence is not therefore essential for the implementation of the present invention. As regards its length, the inventors have observed that a sequence of 6 nucleotides can confer sufficient spacing. Generally, it will be preferred to use a longer sequence, of approximately 10 to 100 nucleotides, and preferably from 50 to 100 nucleotides.

Highly advantageously, a spacer sequence which allows the insertion of a hammerhead ribozyme at the 5' end of the genomic RNA will be used.

Hammerhead ribozymes are small ribozymes (generally of approximately 40 to 80 nucleotides) which have in common a secondary structure made up of 3 helices, the size and the sequence of which can vary, connected by a conserved central core which is essential for the catalytic activity (RUFFNER et al., Biochemistry, 29, 10695-10702, 1990).

A sequence which allows the insertion of a hammerhead ribozyme at the 5' end of the genomic RNA of a Salmonidae alphavirus can be defined by general formula (I) herein after:

5' $X_1$CTGANGAR$X_2B_2X'_2$YGAAA$X_3B_3X'_3$TH (3') (SEQ ID NO: 25)

in which A, T, G, and C have their usual meaning; H represents C, T or A; R represents A or G; Y represents C or T; N represents A, T, G or C; $X_1$ represents an oligonucleotide of at least 3 nucleotides, preferably from 6 to 10 nucleotides, of sequence complementary to that of the 5' end of the genome of said alphavirus; $X_2$ represents an oligonucleotide of at least 3 nucleotides, preferably from 3 to 5 nucleotides, of any sequence; $B_2$ represents an oligonucleotide of 4 or 5 nucleotides, of any sequence; $X'_2$ represents an oligonucleotide complementary to $X_2$; $X_3$ represents an oligonucleotide of at least 2 nucleotides, preferably of 6 to 10 nucleotides, of any sequence; $B_3$ represents an oligonucleotide of 4 to 5 nucleotides, of any sequence; $X'_3$ represents an oligonucleotide complementary to $X_3$.

In order to ensure correct termination of the alphavirus RNA when a bacteriophage promoter is used, the recombinant DNA in accordance with the invention will also comprise, conventionally, the transcription terminator which corresponds to the promoter used. When a promoter recognized by an endogenous RNA polymerase of the host cell is used, a polyA tail, fused to the 3' end of the viral genome, is used.

The recombinant DNAs in accordance with the invention can be readily constructed from the cDNA obtained by reverse transcription of the genomic RNA of the Salmonidae alphavirus chosen. If desired, various modifications can be made to this cDNA, according to the use envisioned for the recombinant DNA in accordance with the invention. This may, for example, involve the introduction of one or more restriction sites, the deletion of portions of the viral genome, in particular of portions not required for its replication (for example, all or part of the region encoding the structural proteins), the duplication of viral sequences, the insertion of heterologous sequences, etc. It may also involve mutations whose effects on the properties of these alphaviruses, for example on their infectious capacity, their pathogenicity of their antigenicity, it is desired to test.

The expressions "cDNA of the genomic RNA of a Salmonidae alphavirus" or "cDNA of a Salmonidae alphavirus", used here, should be interpreted as encompassing both the cDNA obtained by reverse transcription of the genomic RNA of said alphavirus, and the cDNA modified as indicated above.

The present invention thus makes it possible to carry out the manipulation of the Salmonidae alphavirus genome, with a view to various applications, and to produce, in large amounts and reproducibly, the Salmonidae alphaviruses thus obtained.

The present invention makes it possible in particular to construct, from Salmonidae alphaviruses, expression vectors of structure similar to those already constructed from other alphaviruses (for review, cf., for example, FROLOV et al., Proc. Natl. Acad. Sci. USA, 93, 11371-11377, 1996). These expression vectors may be of two main types:

vectors capable of replicating, of expressing the heterologous sequence which is inserted therein, and of becoming encapsidated so as to produce new viral particles. These vectors are generally obtained from the complete genome of an alphavirus by inserting into the latter the heterologous sequence of interest placed under the control of a copy of the subgenomic promoter;

vectors capable of replicating and of expressing the heterologous sequence which is inserted therein, but incapable of producing new viral particles. These vectors are generally obtained by replacing the region of the alphavirus genome encoding the structural proteins with the heterologous sequence of interest. The encapsidation of the virus can only take place if the structural proteins are provided in trans in the host cells, for example due to the introduction into said cells of helper vectors expressing these proteins, or due to the use, as host cells, of cell lines stably transformed with expression cassettes expressing these proteins.

Recombinant DNAs in accordance with the invention can thus be used for the expression of a heterologous sequence of interest under the control of a subgenomic promoter of a Salmonidae alphavirus. In this case, the Salmonidae alphavirus cDNA insert contains one or more expression cassette(s), each of which contains: a copy of said subgenomic promoter and, downstream of said subgenomic promoter and under the transcriptional control thereof, a heterologous sequence that it is desired to express, or a cloning site for the insertion of this sequence.

The subgenomic promoter of alphaviruses is recognized by the nsP complex, and controls the transcription of the genes encoding the structural proteins. In Salmonidae alphaviruses, this promoter is located in the region of the genome comprising the end of the sequence encoding nsp4, and the junction region (in the case of SDV, this promoter is located in the region corresponding to nucleotides 7686-7846 of the genome, comprising the last 124 nucleotides of the sequence encoding nsp4, and the junction region).

The heterologous sequence may be a sequence encoding a protein of interest, or else a sequence transcribed into an RNA of interest, for example an antisense RNA or an interfering RNA.

A subject of the present invention is also a method for obtaining an RNA of a Salmonidae alphavirus, characterized in that it comprises the introduction of a construct in accordance with the invention into an appropriate host cell, and the culturing of said host cell.

The host cells that can be used in the context of the present invention are preferably fish cells; by way of nonlimiting examples, mention will be made of BF-2 (ATCC CCL-91), CHSE214 (ATCC CCL55) or RTG-2 (ATCC CRL-1681) cells. If necessary, these cells are transformed, transiently or stably, with a construct expressing an RNA polymerase which recognizes the promoter used for the construction of the recombinant DNA in accordance with the invention.

The subject of the present invention is also a method for obtaining a Salmonidae alphavirus RNA replicon, characterized in that it comprises the introduction, into an appropriate host cell, of a recombinant DNA in accordance with the invention in which the spacer sequence is a hammerhead ribozyme sequence defined by general formula (I), and the culturing of said host cell.

The term: "RNA replicon" here defines an RNA molecule capable of replicating autonomously in a host cell.

For the production of recombinant alphaviruses, it is necessary for all of the structural proteins required for encapsidation to also be expressed in the host cell. This expression can be carried out in cis (all the genetic information required for the expression of these proteins is carried by the alphavirus RNA replicon), or else in trans (the alphavirus RNA replicon does not carry all the genetic information required for the expression of these proteins, and the genetic information that is missing is provided by the host cell).

If the recombinant DNA in accordance with the invention contains all the genetic information required for encapsidation, the RNA replicon produced can be encapsidated in the host cell, so as to produce recombinant Salmonidae alphaviruses capable of penetrating into other cells, of replicating their genome and of becoming encapsidated in said cells autonomously. Such viruses are defined here as "infectious viruses".

If the recombinant DNA in accordance with the invention does not contain all the genetic information required for encapsidation (in particular if it lacks all or part of the region encoding the structural proteins), the RNA replicon produced cannot become encapsidated in the host cell, unless said cell provides, in trans, the genetic information for complementing the deficient encapsidation function (for example, if it is transformed, transiently or stably, with a construct expressing the missing structural proteins). In the latter case, recombinant Salmonidae alphaviruses can be produced in said host cell. They are capable of penetrating into other cells and of replicating their genome in said cells, but may become encapsidated therein only if, like the initial host cell, said cells can trans-complement the deficient encapsidation function. Such viruses are defined here as "abortive viruses".

The subject of the present invention is also the transcripts, and also the Salmonidae alphavirus RNA replicons and the infectious or abortive recombinant Salmonidae alphaviruses, that can be obtained, as described above, from the recombinant DNAs in according to the invention.

The present invention encompasses more particularly the RNA replicons, and the recombinant Salmonidae alphaviruses, that can be obtained from recombinant DNAs in accordance with the invention in which one or more modifications have been introduced, as indicated above, into the cDNA of the alphavirus.

The recombinant expression DNAS, the RNA expression replicons and the recombinant expression Salmonidae alphaviruses in accordance with the invention can be used to obtain vaccines, for example to obtain attenuated or inactivated Salmonidae alphavirus vaccinal strains.

A subject of the present invention is also the vaccines comprising a recombinant DNA, an RNA replicon or a recombinant Salmonidae alphavirus in accordance with the invention, or that can be obtained therefrom. These vaccines can be used in particular for protecting Salmonidae against alphavirus infections.

The present invention will be understood more clearly from the further description which follows, which refers to nonlimiting examples illustrating the obtaining of a recombinant DNA, of RNA replicons and of recombinant viruses in accordance with the invention, from SDV.

EXAMPLES

Viruses and Cells

The viruses used in the examples which follow are derived from the S49P strain of SDV, previously described (CASTRIC et al., Bulletin of the European Association of Fish Pathologists, 17, 27-30, 1997).

These viruses are propagated on monolayer cultures of BF-2 cells, cultured at 10° C. in Eagle's minimum essential medium (EMEM, Sigma FRANCE) buffered at pH 7.4 with Tris-HCl and supplemented with 10% fetal calf serum. In order to obtain a better yield during the transfections, the BF-2 cells used are derived from subclones selected on the basis of their ability to be efficiently transfected.

This selection was carried out as follows:

BF-2 cells were cultured in a 96-well plate, at a rate of one cell per well. After one month, 24 of the clones thus obtained were selected randomly, and amplified in two 12-well plates. Each of these clones was transfected with a test plasmid (pcDNA3-G), obtained by insertion of the sequence encoding the glycoprotein G of the VHSV virus (Viral Haemorrhagic Septicaemia Virus) into the vector pcDNA3 (InVitrogen), downstream of the CMV promoter and of the T7 promoter. The efficiency of the transfection was determined by evaluating the level of expression of the glycoprotein G under the control of the CMV promoter, by immuno-fluorescence, using an antibody directed against this protein.

The eleven clones in which the fluorescence was the strongest were selected and amplified. Each of these clones was again tested, as indicated above, for its ability to be transfected with pcDNA3-G, but, this time, after prior infection with vTF7-3 (FUERST et al., Proc. Natl. Acad. Sci. USA 83, 8122-8126, 1986), and by evaluating the level of expression of the glycoprotein G under the control of the T7 promoter. Finally, 5 clones were selected for their ability to be infected with vTF7-3, combined with their ability to be transfected efficiently.

Amplification Primers:

The sequences of the primers used in the examples which follow are indicated in Table I hereinafter.

TABLE 1

| Primer | Sequence (5'-3')* | Restriction site | SEQ ID NO: |
|---|---|---|---|
| P1 | CC<u>GAATTC</u>GTTAAATCCAAAA GCATACATATATCAATGATGC | EcoRI | 1 |
| P2 | C<u>CCGGGG</u>CGGCCCCAAGGTCG AGAACTGAGTTG, | SmaI | 2 |
| P3 | C<u>CCCGGG</u>AGGAGTGACCGACT ACTGCGTGAAGAAG | SmaI | 3 |
| P4 | GG<u>TCTAGA</u>GTATGATGCAGAA AATATTAAGG | XbaI | 4 |

TABLE 1-continued

| Primer | Sequence (5'-3')* | Restriction site | SEQ ID NO: |
|---|---|---|---|
| P5 | CCTCTAGACCAACCATGTTTC CCATGCAATTCACC | XbaI | 5 |
| P6 | <u>CCGCGG</u>CCGCATTGAAAATTT TAAAAACCAATAGATGACTCA | NotI | 6 |
| 5'RIBO | <u>GGATCC</u>TGGATTTATCCTGAT GAGTCCGTGAGGACGAAACTA TAGGAAAGGAATTCCTATAGT CGATAAATCCAAAAGC | BamHI | 7 |
| 3'RIBO | <u>GCCGGC</u>GAAGGGTTAGCTGT GAGATTCTGCATCATTGATAT ATGTATGCTTTTGGATTTATC GACTATAGGAATTCCTT | NaeI | 8 |
| 5'SanDI | CCTCGTCAGC<u>GGGACCC</u>ATAA TGCC | SanDI | 9 |
| 3'?XbaIBlpI | CC<u>GCTGAGC</u>GGTTGGTTGAGA GTATGATGC | BlpI | 10 |
| 5'GFP | CCAACC<u>GCTGAG</u>CATGGTGAG CAAGGGCGAGG | BlpI | 11 |
| 3'GFP | *GTGGCTAACGGCAGGTGATTC ACGCTTAAGCTCGAGATCTGA GTCCG* | – | 12 |
| 5'nsp4 | *GCGTGAATCACCTGCCGTTAG CCACAATGGCGATGGCCACGC TCG* | – | 13 |
| 3'Jun | CCAT<u>GCTGAG</u>CGCTTGGTTGA GAGTATGATGC | BlpI | 14 |
| nsP4-F | GGCGGCTTCCTGTTACTCGAC ACGG | – | 15 |
| 5'ProGFP | ATCGATGAAC<u>GATATC</u>GGCCG CCGCTACACGCTATGGCG | EcoV | 16 |
| 3'ProGFP | CCGGAT<u>GCTAGC</u>TTAAGCTCG AGATCTGAGTCCG | NheI | 17 |
| 3'UTR | CGAGCTTAA<u>GCTAGC</u>ATTCCG GTATACAAATCGC | NheI | 18 |
| T7t | GGCTAGGTCG<u>GCGGCCGC</u>AAA AAACCCCTCAAGACCCG | NotI | 19 |
| GSP1 | CCGCCGAGTCGCTCCAGTTGG CG | – | 20 |
| GSP2 | CGGGTTCTCCAGGACGTCCTT CAAG | – | 21 |
| 5'RACEseq | GGCGGCGGCATGGTCGTTGGA CGACCGG | – | 22 |
| Cap-R | CCTTCAGCATAGTCATGGCCT TCTTTGG | – | 23 |
| GFP-R | TTAAGCTCGAGATCTGAGTCC GGAC | – | 24 |

The restriction sites are underlined. The sequences in italics are part of the nsP4 sequence and the sequences indicated in bold are part of the GFP sequence.

Example 1

Cloning of the Complete SDV Genome

A whole SDV cDNA construct, pBS-VMS, was obtained from cDNA fragments (numbered 1 to 3) covering the complete SDV genome, obtained from the previously published sequence (VILLOING et al., 2000; WESTON et al., 2002, mentioned above; GENBANK accession number: NC_003433.1/GI:19352423). Each fragment was amplified by reverse transcription followed by PCR (RT-PCR) using the SDV genomic RNA as template. The RNA was extracted using the QIAamp viral RNA purification kit (Qiagen), from the PEG-concentrated supernatants of SDV-infected cells. The primers (P1 to P6) used for the reverse transcription and the PCR amplification are given in Table 1.

The cDNA fragments obtained were ligated to one another and assembled at the multiple cloning site of the pBlueScript plasmid using the EcoRI, SmaI, XbaI and NotI restriction sites. The plasmid obtained is represented in FIG. 1.

As indicated in FIG. 1, an XbaI restriction site was introduced artificially so as to facilitate subsequent cloning steps. The sequencing of the pBS-VMS construct demonstrated 42 variations compared with the published sequence. These variations are listed in table II hereinafter, and indicated by the letters (a to x) on the pBS-VMS construct represented in FIG. 1. The sequences in FIG. 1 are disclosed as SEQ ID NO: 26 and 30, respectively, in order of appearance.

Among them, 8 chance mutations were corrected as follows: various portions of the SDV RNA genome corresponding to the regions of the cDNA genome containing the mutations were re-amplified by RT-PCR. Each PCR product was sequenced and, if its sequence was correct, was inserted in place of its homolog into the pBS-VMS construct using the appropriate restriction sites and standard technology (SAMBROOK et al., Molecular cloning: a laboratory manual, 2nd ed. Cold Spring Harbor Laboratory Press. Cold Spring Harbor, N.Y., 1989). With the exception of the XbaI restriction site, the final pBS-VMS construct contains an exact cDNA copy of the SDV RNA genome.

TABLE II

| | Position (nt) | | Nucleotide* | Amino acid* |
|---|---|---|---|---|
| 5'UTR | 2 | a | T? A | |
| nsP1 | 35 | b | T? A | L? Q |
| | 1123 | c | G? A | D? N |
| | 1519 | d | G? A | G? R |
| | 1531 | d | C? A | L? I |
| nsP2 | 1958 | | C? A | A? D |
| | 2345 | | G? A | G? E |
| | 2477 | | A? G | E? G |
| | 2669 | | T? C | L? P |
| | 3728 | e | G? C | R? P |
| | 3934 | f | CG? GT | R? V |
| | 3938 | f | G? T | R? L |
| | 3941 | f | C? T | S? F |
| nsP3 | 5084 | | C? T | P? L |
| | 5095 | | A? G | I? V |
| nsP4 | 6107 | g | T? C | L? P |
| | 6392 | | T? A | F? Y |
| | 6471 | h | A? C | E? D |
| | 6505 | i | A? G | K? E |
| | 7467 | j | A? C | E? D |
| jun | 7836 | | CA? AG | |
| Capsid | 8337 | k | T? A | F? I |
| | 8383 | l | T? A | V? D |
| | 8415 | m | T? A | C? S |
| | 8469 | n | G? T | G? W |
| | 8482 | o | A? C | N? T |
| | 8486 | o | T? — | Frameshift |
| | 8490 | o | G? — | |
| | 8504 | p | T? G | |
| | 8506 | p | T? C | |
| | 8510 | p | T? A | |
| | 8539 | q | G? — | |
| | 8553-55 | r | CcA? GcC | P? A |
| | 8556 | r | T? A | F? I |

TABLE II-continued

| Position (nt) | | Nucleotide* | Amino acid* |
|---|---|---|---|
| E2 | 9310 | s | C? T | T? M |
| | 9937 | t | T? G | L? W |
| 6K | 10422 | u | GCG? AGC | A? S |
| E1 | 10858 | | A? G | E? G |
| | 11709 | v | A? G | R? G |
| | 11722 | w | A? — | Frameshift |
| | 11739 | w | T? — | |
| | 11751 | x | G? — | |

*The first position corresponds to the published sequence; the second position corresponds to the cDNA sequence determined in the present study. The accidental mutations that were corrected are indicated in bold. The letters (a-x) refer to FIG. 1

Example 2

Construction of a Genomic RNA Allowing the Synthesis of the Nonstructural SDV Proteins in Fish Cells, and of an SDV Replicon Expressing GFP and Luciferase The SDV CDNA insert was transferred from pBS-VMS into a vector pcDNA3 (Stratagene) between the EcoRI and NotI restriction sites, downstream of the cytomegalovirus (CMV) immediate early (IE) promoter and of a T7 RNA polymerase promoter. The resulting construct was called pSDV.

The region of the cDNA encoding the structural proteins was removed by digestion with XbaI, one site of which is in the junction region and the other of which is in the multiple cloning site of pDNA3, downstream of the cDNA. The construct was autoligated to give the plasmid p-nsP, represented in FIG. 2A).

Figure 2B:
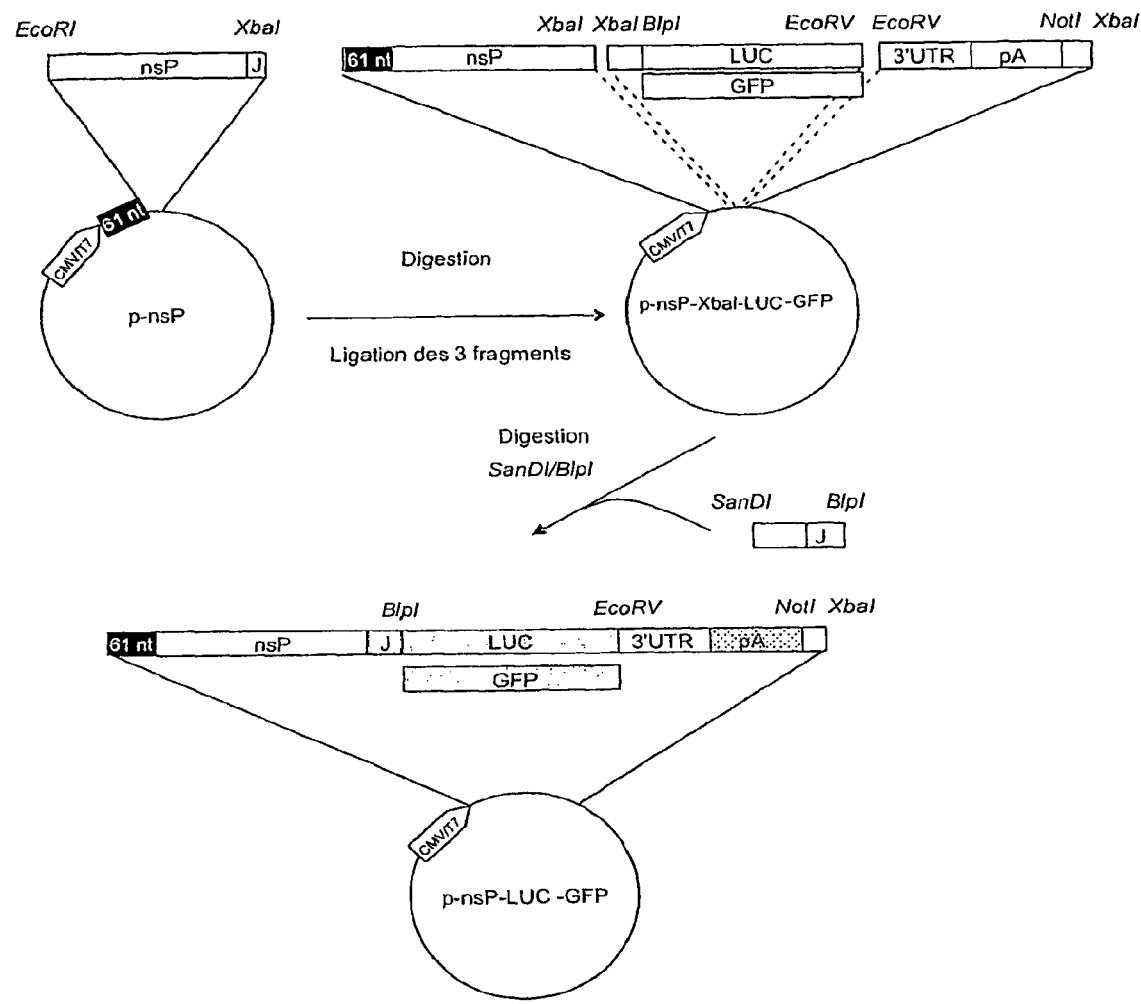

The plasmid p-nsP was then linearized with XbaI in order to insert, downstream of the region encoding the nonstructural proteins, a sequence encoding GFP or luciferase (LUC) preceded by the end of the junction region and[2] followed by the 3' untranslated end of SDV fused to a poly (A) tail. The artificial XbaI site of the junction region was removed by interchanging a SanDI/BlpI fragment. The reading frame of GFP or that of luciferase is bordered by two unique restriction sites: an EcoRV site and a BLPI site. In these final constructs, called p-nsp-GFP and p-nsp-LUC, the CMV/T7 promoter combination is separated from the 5' end of the SDV genome by 61 nucleotides belonging to the multiple cloning site of pcDNA3. These constructs are represented in FIG. 2B.

In order to evaluate the functionality of these constructs for the expression of the GFP and LUC reporter genes, each of them was used to transfect BF-2 cells, which were incubated at 10° C., in culture plate wells (6×10⁵ cells/well), and the luciferase activity and GFP activity were measured daily.

To measure the luciferase activity, the transfected cells were harvested before measurement, washed with PBS, and lysed with 75 μl of 1× lysis buffer (25 mM Tris-phosphate (pH 7.8), 2 mM DTT, 2 mM 1,2-diaminocyclohexane-N,N,N',N'-tetraacetic acid, 10% glycerol, 1% Triton X-100). The lysates are clarified by low-speed centrifugation, and the proteins are quantified by the Bradford method, in order to normalize the samples.

50 μl of luciferase reagent (Promega) are added to aliquots of the clarified lysates.

In the case of GFP, the expression in the transfected cells is directly monitored by observation under a microscope in UV light.

The expression of the nonstructural proteins is detected by immunofluorescence from the day after transfection onward.

On the other hand, respective of the time-after transfection, neither luciferase activity nor GFP fluorescence is detected.

The results are given in table III below.

TABLE III

| Plasmid construct | Expression of nonstructural proteins | GFP expression | Luciferase expression |
|---|---|---|---|
| p-nsP-GFP | +++ | – | |
| p-nsP-LUC | +++ | | – |

These results indicate that the viral RNA was transcribed, but that no expression of the GFP or luciferase reporter genes, which are placed under the control of the SDV 26 Subgenomic promoter, is observed.

This makes it possible to suppose that the replicative viral complex is not functional due to the fact that the 5' end is not strictly identical to that of the SDV genome.

Use of a Ribozyme as Spacer:

A hammerhead ribozyme sequence (HH sequence) was fused to the first nucleotide of the 5' end of the SDV cDNA genome, in the following way: a HindIII fragment of p-nsP, containing the first two Kb of SDV cDNA was removed and subcloned into a plasmid pUC19, to give the construct pUC-SDV HindIII. A BamHI/NaeI fragment containing the 5' end of the SDV genome was removed from this construct, and was replaced with a synthetic DNA fragment generated by hybridization of two partially complementary oligonucleotides of 79 and 80 nucleotides comprising the sequence of the hammerhead ribozyme fused to the 5' end of the SDV genome, and filling using the T4 DNA polymerase Klenow fragment. The sequence of these oligonucleotides (5'RIBO and 3'RIBO) is given in table I.

Figure 3A:
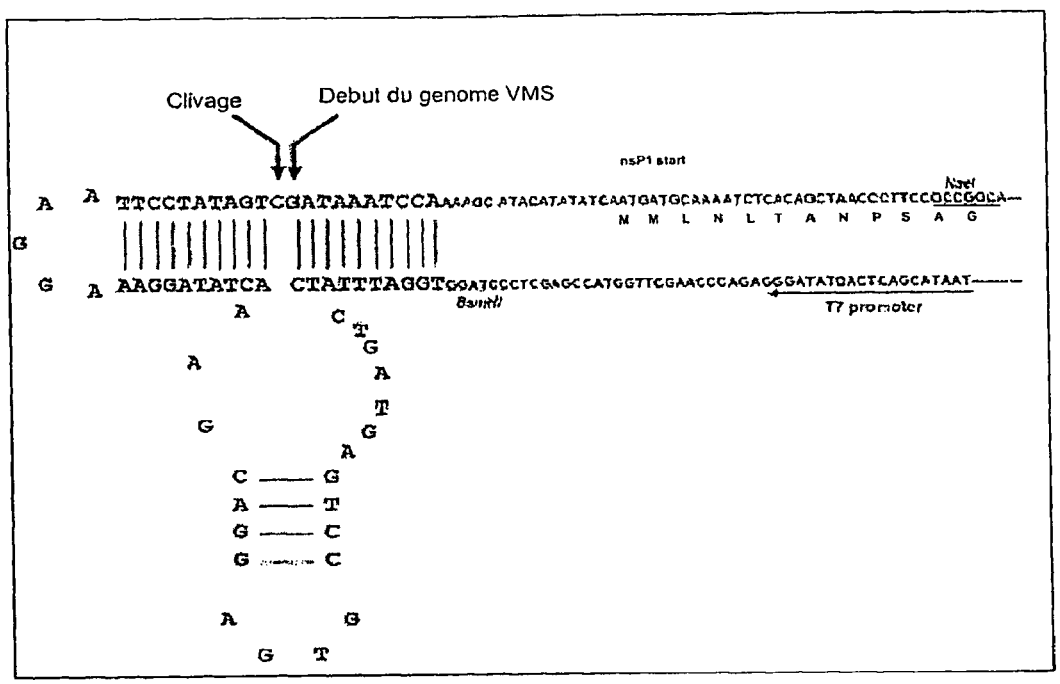

The sequence of the hammerhead ribozyme is represented in FIG. 3A; the BamHI and NaeI sites and the T7 promoter are underlined. The ribozyme cleavage site and the start of the SDV genome are indicated by arrows. The nucleotide and protein sequences in FIG. 3A are disclosed as SEQ ID NO: 27 and 28, respectively, in order of appearance.

After digestion with the appropriate restriction enzymes, the synthetic DNA fragment was inserted into the plasmid pUC-SDV HindII, to give the construct pUC-HH-SDV HindIII. The modified HindIII fragment was recovered from this construct and reinserted into the plasmid p-nsP, to give the construct pHH-nsP.

Figure 3B:
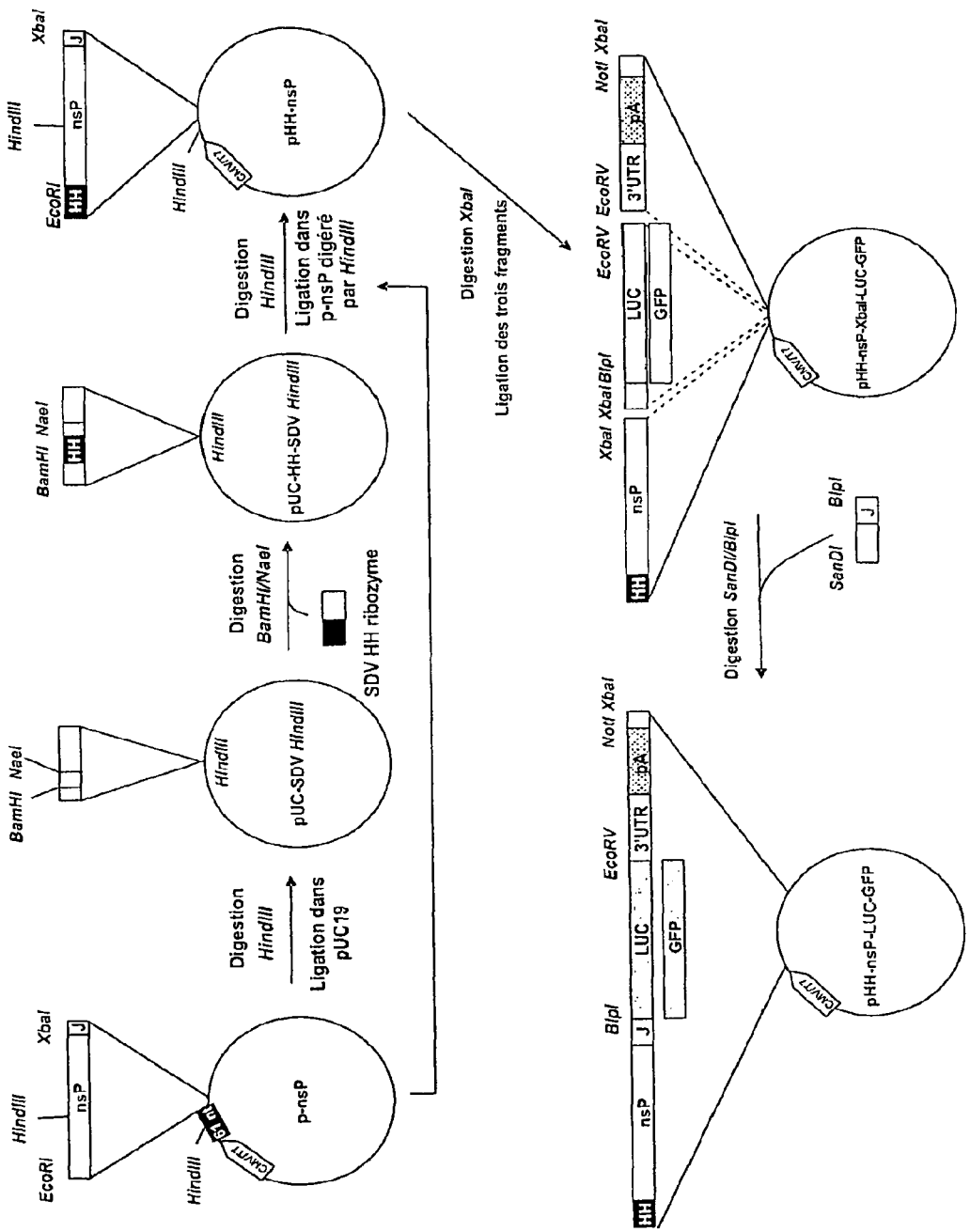

The resulting construct pHH-nsP was then linearized with XbaI and modified in the same way as in the case of p-nsP: insertion, downstream of the region encoding the nonstructural proteins, of a sequence encoding GFP or luciferase (LUC) bordered by the BlpI and EcoRV sites, preceded by the end of the junction region and followed by the 3' untranslated end of SDV fused to a poly (A) tail, correction of the artificial XbaI site. The final constructs are called pHH-nsP-GFP and pHH-nsP-LUC. The steps for obtaining these constructs are given in FIG. 3B.

The functionality of these constructs was evaluated in the same way as for the constructs p-nsP-GFP and p-nsP-LUC.

Figure 4:
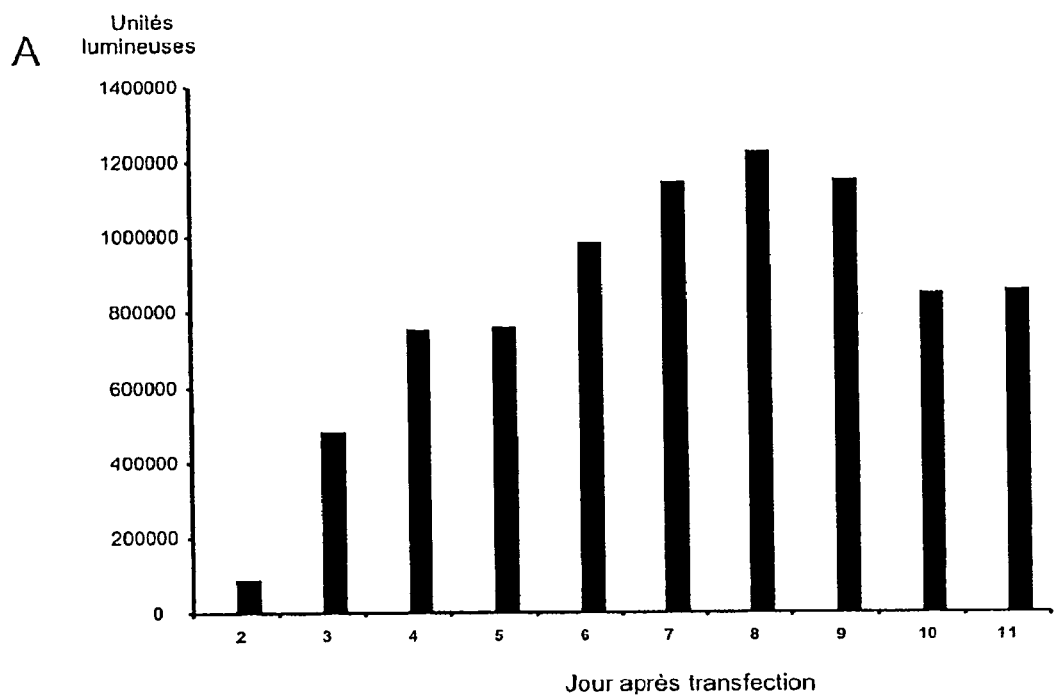
Figure 4:
Figure 4:
Figure 4:
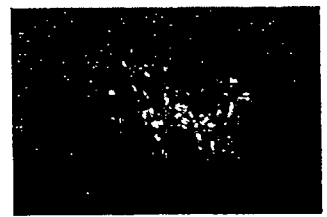

The results are illustrated in FIG. 4.

A significant luciferase activity is detected from 2 days after infection onward, and increases up to 9 days after transfection (FIG. 4A). GFP expression is demonstrated 4 days after transfection, and is optimal, as for luciferase, after 9 days (FIG. 4B).

These results indicate that the SDV replicase complex (nsP1, nsP2, nsP3 and nsP4) expressed from the pHH-nsP-LUC or -GFP vectors is biologically active and is capable of replicating and of transcribing a subgenomic RNA containing the reporter genes. These data also show that the cleavage of the 5' end of the SDV genome was effectively carried out by the hammerhead ribozyme.

Example 3

Construction of an Infectious Recombinant cDNA of SDV

An infectious SDV cDNA clone was constructed in the following way:

The region encoding the structural proteins of SDV was inserted between the BlpI and EcoRV sites of pHH-nsP-LUC, as a replacement for the sequence encoding luciferase, to give the construct pHH-SDV.

Figure 5:
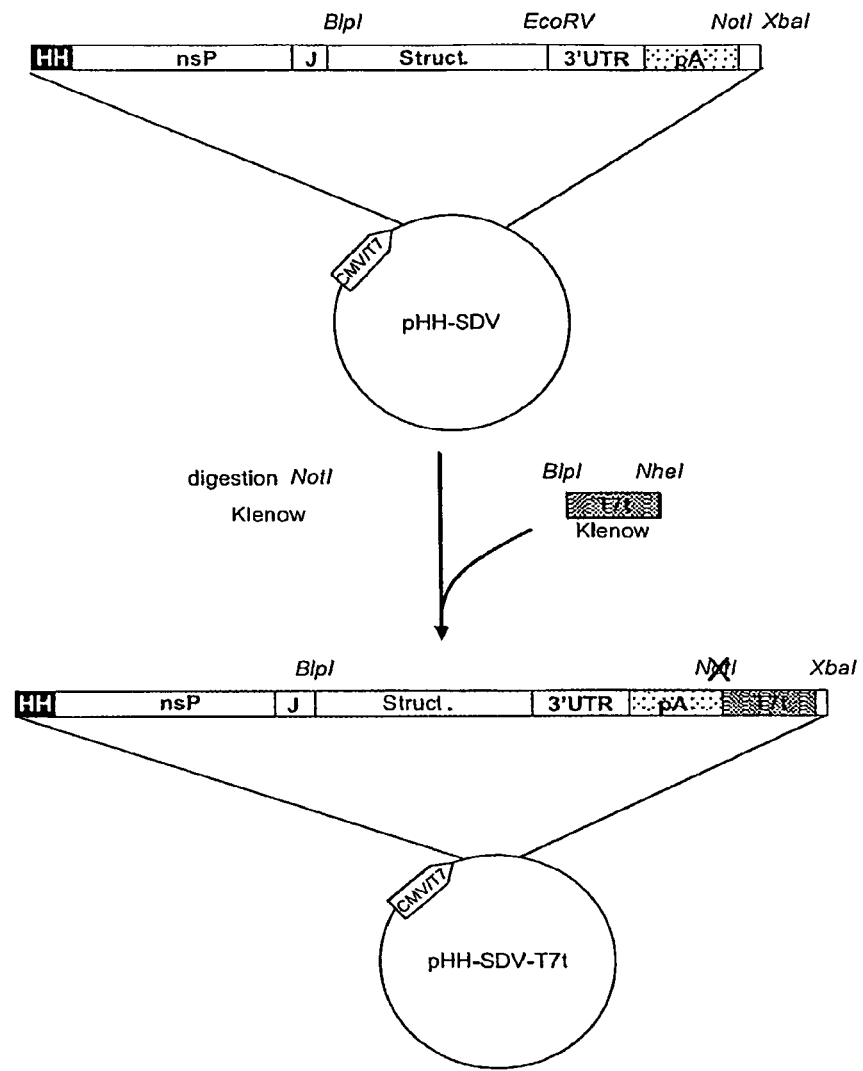
Figure 7:
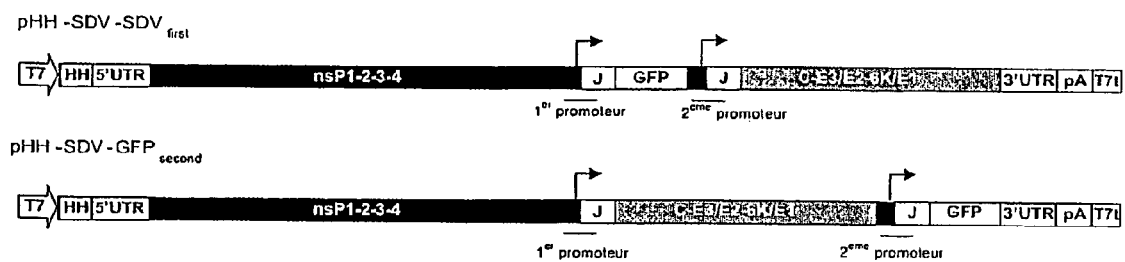
Figure 7:
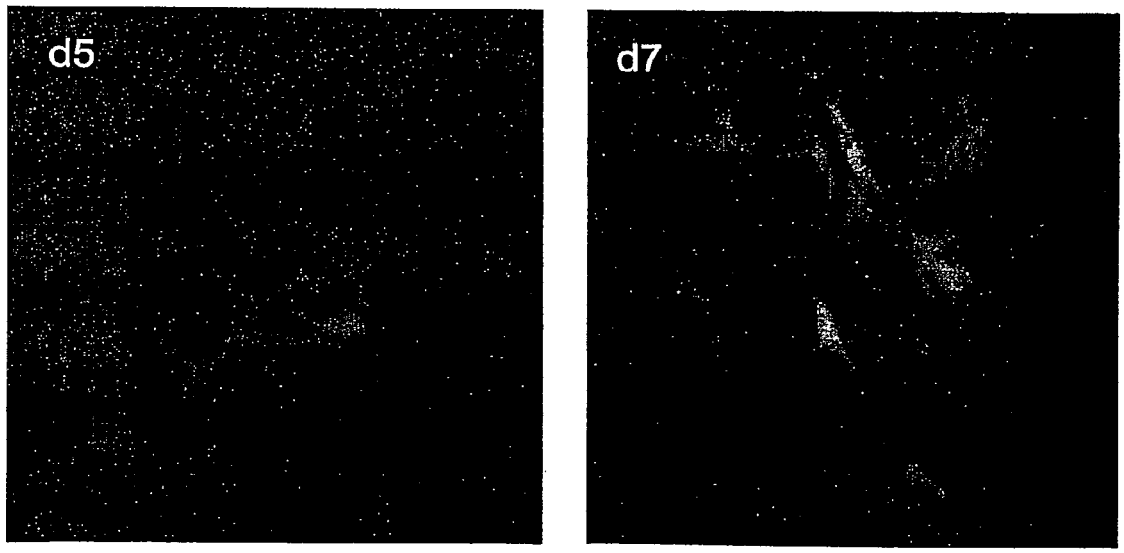
Figure 8:
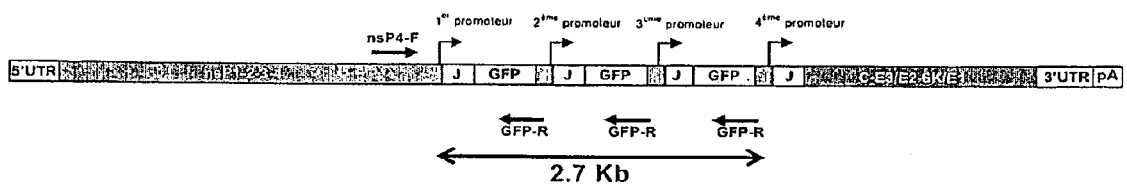
Figure 8:
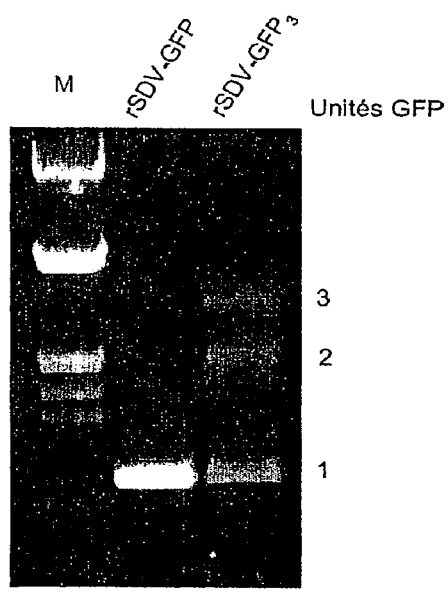

This construct was also modified by insertion of a T7 terminator (T7t): the pHH-SDV vector was linearized by digestion with the NotI restriction enzyme, and blunt-end ligated with a BlpI/NheI fragment of the vector pET-14b (Novagen) containing a T7 terminator (prior to the ligation, the ends of the two fragments were filled using the T4 DNA polymerase Klenow fragment). The resulting construct is called pHH-SDV-T7t. The steps for obtaining this construct are shown schematically in FIG. 5.

This construct was used to transfect BF-2 cells infected with the recombinant vaccinia virus vTF7-3, which expresses the T7 RNA polymerase (FUERST et al., 1986, mentioned above). The BF-2 cells (approximately $1.2 \times 10^6$ cells/well) are cultured in 12-well plates and infected with vTF7-3 (multiplicity of infection=5). After 1 hour of adsorption at 37° C., the cells are washed twice, and transfected with 1.6 µg of PSDV, using the Lipofectamine 2000 reagent, according to the manufacturer's instructions (Invitrogen). The cells are incubated for 7 hours at 37° C. and washed with MEM medium before being transferred to 10° C. and incubated at this temperature for 7 or 10 days. In certain experiments, transfections were carried out according to the same protocol, but without prior infection of the cells with vTF7-3.

7 days and 10 days after transfection, the cells are fixed with a 1/1 alcohol/acetone mixture at 20° C. for 15 minutes, and incubated with an assortment of monoclonal antibodies directed against structural or nonstructural proteins of SDV, said antibodies being diluted to 1/1000 in PBS-Tween. After incubation for 45 minutes at ambient temperature, the cells are washed and incubated with an anti-mouse immunoglobulin antibody (Biosys, France). After washing, the cells are examined with a m microscope under UV light.

In parallel, the supernatants are recovered, clarified by centrifugation at 10 000×g in a microcentrifuge, and used to infect fresh BF-2 cells, cultured at 10° C. as a monolayer in 24-well plates. The cells thus infected are analyzed by immunofluorescence as described above.

Figure 6:
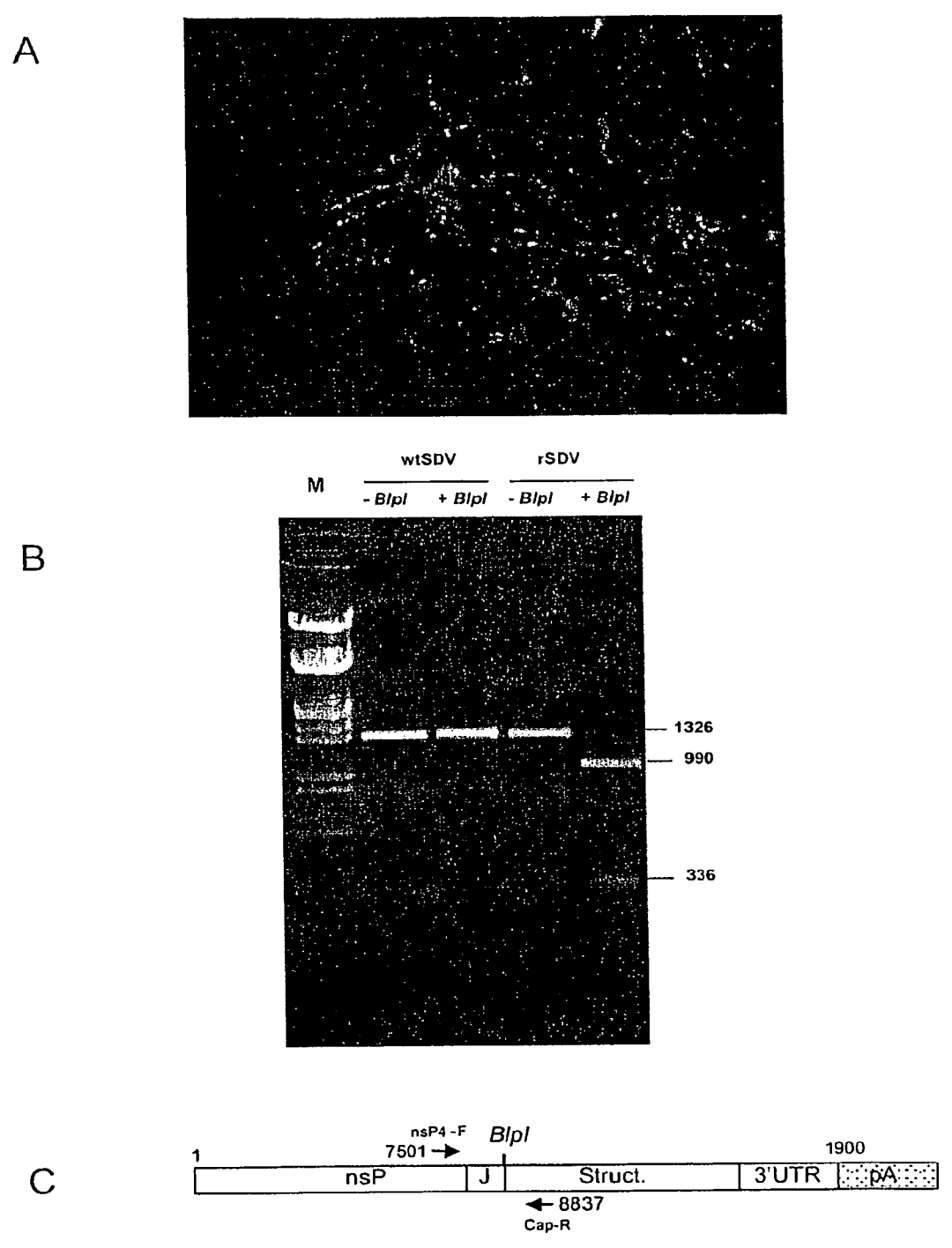

The results observed 7 days after transfection are shown in FIG. 6A: some small loci appear; they are greater in size 10 days after infection, which probably reflects a cell-to-cell infection by the recombinant SDV.

The recombinant SDV has a BlpI restriction site, which is absent from the wild-type virus. In order to verify that the virus produced by the infected cells is indeed the recombinant SDV, the RNA is extracted from the cells infected with the recombinant SDV, after the first passage, and used as a template to carry out an RT-PCR using the primers NsP4-F and CapR, bordering the BlpI site. The position of these primers is indicated in FIG. 6C. An RT-PCR is also carried out, with the same primers, using RNA extracted from cells infected with the wild-type virus.

The amplification products are digested with BlpI, and their restriction profiles are compared. The results are shown in FIG. 6B. In the absence of BlpI (−BlpI), a fragment of 1326 nucleotides is observed with the recombinant SDV, as with the wild-type virus. After digestion with BlpI (+BlpI), this fragment remains intact in the case of the wild-type virus, and gives a fragment of 990 nucleotides and a fragment of 336 nucleotides in the case of the recombinant SDV.

Example 4

In Vivo Infection with the Recombinant SDV

In order to verify the infectious capacity of the recombinant SDV, 50 healthy young rainbow trout (*Oncorhynchus mykiss*) were infected by immersion for 2 hours in an aquarium filled with water at 10° C., containing $5 \times 10^4$ PFU/ml of wild-type SDV or of recombinant SDV, obtained from infected BF-2 cells. The aquarium is then made up to 30 liters with fresh water. Fish used as control are treated under the same conditions, with culture medium in place of the viral suspension.

3 weeks after infection, some fish were sacrificed and homogenates of organs of each fish were used to infect BF-2 cells. Analysis of these cells by immuno-fluorescence, as described in example 3 above, shows the presence of virus in the cells infected with the organ homogenates from fish infected with the wild-type SDV or with the recombinant SDV (results not shown).

All the fish sacrificed were positive for SDV, the viral titer being approximately $10^7$ PFU/ml for the wild-type SDV as for the recombinant SDV.

Example 5

Construction of an Infectious Recombinant SDV Expressing a Heterologous Gene

In order to produce an infectious recombinant virus expressing GFP, the infectious cDNA pHH-SDV-T7t is modified in two different ways, in order to insert an additional expression cassette expressing GFP.

1) Construction of the Infectious cDNA pHH-SDV-GFPfirst

The pHH-nsP-GFP construct is used as template to generate two separate PCR amplification products: the "GFP PCR product is obtained using the 5'GFP and 3'GFP primers (table 1); the "subgenomic SDV PCR" is obtained using the 5'nsP4 (77-6-7750) and 3'Jun primers (table 1). Since the exact location and the minimum size of the SDV subgenomic promoter have not yet been determined, a fragment of approximately 100 nucleotides, containing the end of the sequence of nsP4 and the junction region, was used. The SDV subgenomic promoter is then ligated, by PCR, in a position 3' of the sequence encoding GFP, by mixing the two products derived from the first amplification and using the 5'GFP and 3'Jun primers.

The resulting amplification product (GFP-SDVPro) is digested with BlpI and inserted into the pHH-SDV-T7t construct, digested beforehand with BlpI, so as to obtain the infectious cDNA pHH-SDV-GFPfirst.

2) Construction of the Infectious cDNA pHH-SDV-GFPsecond

In this construct, the GFP expression cassette is inserted downstream of the structural genes.

Two PCR amplification products are generated:
the SDV subgenomic promoter fused to GFP (product PCR1), using as primers 5'ProGFP and 3'ProGFP (table 1), and as matrix the pHH-nsP-GFP construct;

the 3'untranslated region of SDV fused to a poly(A) tail and to the T7 promoter (product PCR2), using as primers 3'UTR and T7t (table 1), and as template the pHHSDV-T7t construct.

The PCR1 and PCR2 products are assembled by PCR using the 5'ProGFP and T7t primers. The PCR amplification product is digested with EcoRV and Notl, and inserted into the PHH-SDV construct digested with the same enzymes, so as to obtain the infectious cDNA pHH-SDV-GFPsecond.

These two constructs are shown schematically in FIG. 7A.

These constructs are used to transfect BF-2 cells infected with vTF7, and the GFP expression is monitored daily. The results are shown in FIG. 7B.

The GFP expression is detectable starting from 7 days after transfection for the two pHH-SDV-GFP constructs. However, a more intense expression of GFP is observed when the GFP gene is located downstream of the structural protein genes in the genome.

During the cloning of the GFP gene into pSDV in order to obtain the pHH-SDV-GFPfirst construct, a plasmid (pHH-SDV-$GFP_3$) suspected of containing 3 GFP cassettes was selected.

This plasmid is shown schematically in FIG. 8A.

An RT-PCR using the nsP4-F and GFP-R primers (table 1) made it possible to confirm that effectively 3 GFP cassettes were present in the pHHSDV-$GFP_3$ plasmid.

The results of this RT-PCR are represented in FIG. 8B. Together, these three GFP cassettes represent a DNA fragment of 2.7 Kb.

This construct was transfected into BF-2 cells infected with vTF7-3, and the appearance of loci of infected cells after 9 days confirmed the functionality of this construct.

These results show that SDV can contain a heterologous nucleic acid which is more than 20% longer than the wild-type virus genome.

The invention claimed is:

1. A recombinant DNA comprising:
a transcription promoter and, downstream of said promoter and under transcriptional control thereof;
a spacer sequence positioned between the transcription promoter and;
a cDNA of a genomic RNA of a Salmonidae alphavirus, wherein the spacer sequence is defined by general formula (I) below:

5' $X_1$CTGANGAR$X_2B_2X'_2$YGAAA$X_3B_3X'_3$TH (I) (SEQ ID NO: 29)

in which A, T, G, and C have their usual meaning; H represents C, T or A; R represents A or G; Y represents C or T; N represents A, T, G or C; $X_1$ represents an oligonucleotide of at least 3 nucleotides, of sequence complementary to that of the 5' end of the genome of said alphavirus; $X_2$ represents an oligonucleotide of at least 3 nucleotides, of any sequence; $B_2$ represents an oligonucleotide of 4 or 5 nucleotides, of any sequence; $X'_2$ represents an oligonucleotide complementary to $X_2$; $X_3$ represents an oligonucleotide of at least 2 nucleotides, of any sequence; $B_3$ represents an oligonucleotide of 4 to 5 nucleotides, of any sequence; $X'_3$ represents an oligonucleotide complementary to $X_3$.

2. The recombinant DNA of claim 1, wherein the Salmonidae alphavirus cDNA contains one or more expression cassette(s), each of which contains: a copy of a subgenomic promoter and, downstream of said subgenomic promoter and under transcriptional control thereof, a heterologous sequence that is desired to express, or a cloning site for the insertion of the heterologous sequence.

3. An immunogenic composition comprising the recombinant DNA of claim 1.

4. An immunogenic composition comprising the recombinant DNA of claim 2.

5. A method for preparing a Salmonidae alphavirus RNA replicon, the method comprising introducing into an isolated host cell the recombinant DNA of claim 1, followed by culturing the isolated host cell.

6. A method of inducing an immune response to Salmonidae alphavirus in a fish, the method comprising introducing the recombinant DNA of claim 2 to a fish.

7. A method for preparing a recombinant Salmonidae alphavirus, the method comprising introducing the recombinant DNA of claim 2 into an isolated host cell in which all of the structural proteins of said Salmonidae alphavirus that are required for encapsidation of the Salmonidae alphavirus are expressed, and culturing of said isolated host cell.

8. The method of claim 7, wherein all genetic information for the expressing said structural proteins is carried by said recombinant DNA.

9. The method of claim 7, wherein all or part of the genetic information for expressing said structural proteins is provided in trans by the isolated host cell.

10. A method for preparing a recombinant Salmonidae alphavirus, the method comprising introducing the recombinant DNA of claim 1 into an isolated host cell in which all of the structural proteins of said Salmonidae alphavirus that are required for encapsidation of the Salmonidae alphavirus are expressed, and culturing of said isolated host cell.

11. A method of inducing an immune response to Salmonidae alphavirus in a fish, the method comprising introducing the recombinant DNA of claim 1 to a fish.

12. A method for preparing a Salmonidae alphavirus RNA replicon, the method comprising introducing into an isolated host cell the recombinant DNA of claim 2, followed by culturing the isolated host cell.

13. A recombinant Salmonidae alphavirus obtained by the method of claim 7.

14. An immunogenic composition comprising the recombinant Salmonidae alphavirus of claim 13.

* * * * *

UNITED STATES PATENT AND TRADEMARK OFFICE
CERTIFICATE OF CORRECTION

PATENT NO. : 8,603,491 B2  
APPLICATION NO. : 11/993676  
DATED : December 10, 2013  
INVENTOR(S) : Leberre et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1278 days.

Signed and Sealed this  
Twelfth Day of May, 2015

Michelle K. Lee  
*Director of the United States Patent and Trademark Office*

```
                         SEQUENCE LISTING

<160> NUMBER OF SEQ ID NOS: 30

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgaattcgt taaatccaaa agcatacata tatcaatgat gc                        42

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccggggcgg ccccaaggtc gagaactgag ttg                                  33

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccccgggagg agtgaccgac tactgcgtga agaag                                35

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggtctagagt atgatgcaga aaatattaag g                                    31
```

```
<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctctagacc aaccatgttt cccatgcaat tcacc                                35

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccgcggccgc attgaaaatt ttaaaaacca atagatgact ca                        42

<210> SEQ ID NO 7
<211> LENGTH: 79
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggatcctgga tttatcctga tgagtccgtg aggacgaaac tataggaaag gaattcctat     60
agtcgataaa tccaaaagc                                                  79

<210> SEQ ID NO 8
<211> LENGTH: 80
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gccggcggaa gggttagctg tgagattttg catcattgat atatgtatgc ttttggattt     60
atcgactata ggaattcctt                                                 80

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cctcgtcagc gggacccata atgcc                                           25

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgctgagcg gttggttgag agtatgatgc                                      30
```

```
<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccaaccgctg agcatggtga gcaagggcga gg                                    32

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtggctaacg gcaggtgatt cacgcttaag ctcgagatct gagtccg                    47

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcgtgaatca cctgccgtta gccacaatgg cgatggccac gctcg                      45

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccatgctgag cggttggttg agagtatgat gc                                    32

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcggcttcc tgttactcga cacgg                                            25

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
atcgatgaac gatatcggcc gccgctacac gctatggcg                             39
```

```
<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccggaatgct agcttaagct cgagatctga gtccg                                35

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgagcttaag ctagcattcc ggtatacaaa tcgc                                 34

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggctaggtcg gcggccgcaa aaacccctc aagacccg                              38

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccgccgagtc gctccagttg gcg                                             23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgggttctcc aggacgtcct tcaag                                           25

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggcggcggca tggtcgttgg acgaccgg                                        28

<210> SEQ ID NO 23
<211> LENGTH: 28
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccttcagcat agtcatggcc ttctttgg                                           28

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ttaagctcga gatctgagtc cggac                                              25

<210> SEQ ID NO 25
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: a, c, g or t
<220> FEATURE:
<221> NAME/KEY: modified_base
<222> LOCATION: (15)
<223> OTHER INFORMATION: a, c, g or t
<220> FEATURE:
<221> NAME/KEY: modified_base
<222> LOCATION: (19)..(33)
<223> OTHER INFORMATION: a, c, g, or t
<220> FEATURE:
<221> NAME/KEY: modified_base
<222> LOCATION: (39)..(63)
<223> OTHER INFORMATION: a, c, g or t
<220> FEATURE:
<223> OTHER INFORMATION: see specification as filed for detailed
      description of substitutions and preferred embodiments

<400> SEQUENCE: 25
nnnnnnnnnn ctgangarnn nnnnnnnnnn nnnygaaann nnnnnnnnnn nnnnnnnnnn        60 nnnth                                                                    65

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atactctcaa cc                                                            12

<210> SEQ ID NO 27
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
```

```
taatacgact cactataggg agacccaagc ttggtaccga gctccctagg tggatttatc    60
ctgatgagtc cgtgaggacg aaactatagg aaaggaattc ctatagtcga taaatccaaa   120
agcatacata tatcaatgat gcaaaatctc acagctaacc cttccgccgg ca           172
```

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Met Met Leu Asn Leu Thr Ala Asn Pro Ser Ala Gly
1               5                   10
```

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(3)
<223> OTHER INFORMATION: a, c, g or t
<220> FEATURE:
<221> NAME/KEY: modified_base
<222> LOCATION: (8)
<223> OTHER INFORMATION: a, c, g, or t
<220> FEATURE:
<221> NAME/KEY: modified_base
<222> LOCATION: (12)..(22)
<223> OTHER INFORMATION: a, c, g or t
<220> FEATURE:
<221> NAME/KEY: modified_base
<222> LOCATION: (28)..(29)
<223> OTHER INFORMATION: a, c, g or t
<220> FEATURE:
<221> NAME/KEY: modified_base
<222> LOCATION: (30)..(36)
<223> OTHER INFORMATION: a, c, g or t
<220> FEATURE:
<223> OTHER INFORMATION: see specification as filed for detailed
      description of substitutions and preferred embodiments

<400> SEQUENCE: 29

```
nnnctganga rnnnnnnnnn nnygaaannn nnnnnn                               36
```

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30

```
atactctaga cc                                                         12
```